(12) United States Patent
Choi

(10) Patent No.: US 10,751,024 B2
(45) Date of Patent: Aug. 25, 2020

(54) STETHOSCOPE WITH TWO PAIR OF HEADSETS

(71) Applicant: Joon Hyeok Choi, Seongnam-si, Gyeonggi-do (KR)

(72) Inventor: Wonsuk Choi, Seongnam-si (KR)

(73) Assignee: Joon Hyeok Choi, Seongnam-si, Gyeonggi-Do (KR)

( * ) Notice: Subject to any disclaimer, the term of this patent is extended or adjusted under 35 U.S.C. 154(b) by 1325 days.

(21) Appl. No.: 14/759,834

(22) PCT Filed: Apr. 7, 2015

(86) PCT No.: PCT/KR2015/003465
§ 371 (c)(1),
(2) Date: Jul. 8, 2015

(87) PCT Pub. No.: WO2016/163566
PCT Pub. Date: Oct. 13, 2016

(65) Prior Publication Data
US 2019/0192108 A1    Jun. 27, 2019

(51) Int. Cl.
*A61B 7/02* (2006.01)
*H04R 1/10* (2006.01)
(Continued)

(52) U.S. Cl.
CPC ............. *A61B 7/026* (2013.01); *A61B 7/02* (2013.01); *H04R 1/1016* (2013.01); *H04R 1/46* (2013.01);
(Continued)

(58) Field of Classification Search
CPC .. A61B 7/026; A61B 7/02; A61B 7/04; H04L 1/1016; H04L 1/46; H04L 1/34; H04L 1/028; H04R 2410/00
See application file for complete search history.

(56) References Cited

U.S. PATENT DOCUMENTS

| 3,790,712 | A | * | 2/1974 | Andries | ................... A61B 7/04 381/67 |
| 4,997,055 | A | | 3/1991 | Grady | |
| 5,650,598 | A | | 7/1997 | Abelson | |

FOREIGN PATENT DOCUMENTS

| CN | 202932940 | 5/2013 |
| JP | 2009-125182 | 6/2009 |
| KR | 10-1402179 | 6/2014 |

OTHER PUBLICATIONS

International Search Report (with English Translation) and Written Opinion dated Jan. 6, 2016 issued in Application No. PCT/KR2015/003465.

* cited by examiner

*Primary Examiner* — Matthew Kremer
*Assistant Examiner* — Avery M Foley
(74) *Attorney, Agent, or Firm* — Paratus Law Group, PLLC

(57) ABSTRACT

A stethoscope according to exemplary embodiments of the inventive concept includes a chestpiece for examining a patient by contacting him on the body, a microphone unit for receiving a doctor's voice, a first headset unit connected to the doctor's ears, and a second headset unit connected to the patient's ears, and a guiding unit guiding the chestpiece and the microphone unit to be each connected to at least one of the first headset unit and the second headset unit. Such the composition of the stethoscope enables the patient to listen to the doctor's voice as well as the auscultation sound gathered through the chestpiece, selectively.

6 Claims, 7 Drawing Sheets

(51) Int. Cl.
*H04R 1/46* (2006.01)
*H04R 1/34* (2006.01)
*H04R 1/02* (2006.01)
(52) U.S. Cl.
CPC ................ *H04R 1/028* (2013.01); *H04R 1/34* (2013.01); *H04R 2410/00* (2013.01)

STETHOSCOPE WITH TWO PAIR OF HEADSETS

CROSS-REFERENCE TO RELATED PATENT APPLICATIONS

This application is a U.S. National Stage Application under 35 U.S.C. 5371 of PCT Application No. PCT/KR2015/003465, filed Apr. 7, 2015, whose entire disclosure is hereby incorporated by reference.

TECHNICAL FIELD

Example embodiments of inventive concepts relate to a stethoscope, and more particularly, to a stethoscope for examining a patient.

BACKGROUND ART

Generally, a stethoscope is a medical device for auscultating for the inside of the human body and diagnosing the illness of patient. It is used to listen to various inner body organs such as intestines and blood flow in arteries and veins as well as lung and heart sounds.

The stethoscope includes an auscultation member for auscultating inside of the human body, a headset for listening to the auscultation sound, and a guiding tube for guiding the auscultation sound by connecting the auscultation member and the headset. The stethoscope having such the structure is used to examine a patient through the auscultation sound received from the headset by the auscultation member on the patient's body.

By the way, a doctor needs to provide his headset to the patient in the case that the patient is willing to listen to the auscultation sound by himself. Accordingly, the doctor should endure inconvenience of sharing his headset with the patient. Also, the doctor may have problems with delivering the examination result or requests for examination when the patient has weak hearing ability.

DETAILED DESCRIPTION OF THE INVENTION

Technical Goal of the Invention

According to an exemplary embodiment, the inventive concept provides a stethoscope being capable of delivering the auscultation sound to a patient as well as to a doctor and easy to deliver doctor's voice to a patient who has weak hearing ability.

Technical Solution of the Invention

According to an exemplary embodiment of the inventive concept, a stethoscope includes a chestpiece for examining a patient by touching him on the body, a first headset unit for delivering the auscultation sound to a doctor's ears and a second headset unit for delivering the auscultation sound to a patient's ears, and a guide unit guiding the chestpiece to be connected to at least one of the first headset unit and the second headset unit.

The stethoscope may further include a microphone unit receiving the doctor's voice and the second headset unit is connected to any one of the chestpiece or the microphone unit by the guiding unit.

The guiding unit includes a lever body prepared among the chestpiece, the first headset unit and the second headset unit and an adjusting lever which is attached to the lever body so as to be rotatable connecting the chestpiece and the first headset unit or the chestpiece and the second headset unit with each other according to the lever rotating position.

The guide unit further includes a connecting member prepared among the chestpiece, the first headset unit and the second headset unit so as to be rotatable and a first guideline and a second guide line connecting the chestpiece and the first headset unit or the chestpiece and the second headset unit alternatively according to the rotation position of the connecting member which are prepared inside the connecting member so as to be separated with each other.

The second headset unit includes a first connecting tube and a second connecting tube each connected to the chestpiece and the microphone unit, and the guiding unit includes a guiding body prepared between the first connecting tube and the second connecting tube so as to be movable and a guide hole formed through the guide body, such that the guide unit may open only any one of the first connecting tube and the second connecting tube.

According to an exemplary embodiment of the inventive concept, a stethoscope includes a chestpiece examining a patient by contacting the patient on the body, a microphone unit receiving doctor's voice, a first headset unit connected to the doctor's ears, a second headset unit connected to the patient's ears, and a guiding unit guiding each of the chestpiece and the microphone unit to at least any one of the first headset unit and the second headset unit.

The guiding unit includes a lever body prepared among the chestpiece, microphone unit, the first headset unit and the second headset unit and an adjusting lever installed in the lever body so as to be rotatable between a first position which the chestpiece and the second headset unit, and the microphone unit and the second headset unit are mutually connected, and a second position which the chestpiece and the second headset unit, and the microphone unit and the first headset unit are mutually connected.

The guiding unit further includes a connecting member prepared among the chestpiece, the microphone unit, the first headset unit and the second headset unit so as to be rotatable and a first guide line and a second guide line connecting the chestpiece and the first headset unit, and the microphone unit and the second headset unit mutually, or the chestpiece and the second headset unit, and the microphone and the first headset unit mutually according to the rotating position of the connecting member, which are prepared inside the connecting member while being divided with each other.

The second headset unit includes a first connecting tube and a second connecting tube each connected to the chestpiece and the microphone unit, and the guiding unit includes a guide body prepared between the first connecting tube and the second connecting tube so as to be movable and a guide hole formed through the guide body.

Effect of the Invention

According to the inventive concept, a stethoscope enables a patient to listen to the auscultation sound as well as for a doctor.

The doctor may not have inconvenience of providing his headset to the patient by providing a separate headset to the patient.

A guiding unit enables to guide the auscultation sound to the doctor or the patient as required with simple handle, thereby treatment convenience being improved.

The stethoscope enables a patient having low hearing ability to listen to the doctor's voice and the auscultation sound.

The stethoscope may contribute to increase of treatment reliability according to the listening of the auscultation sound by the doctor and the patient at the same time.

BEST MODE FOR CARRYING OUT THE INVENTION

Various example embodiments will be described more fully hereinafter with reference to the accompanying drawings.

Figure 1:
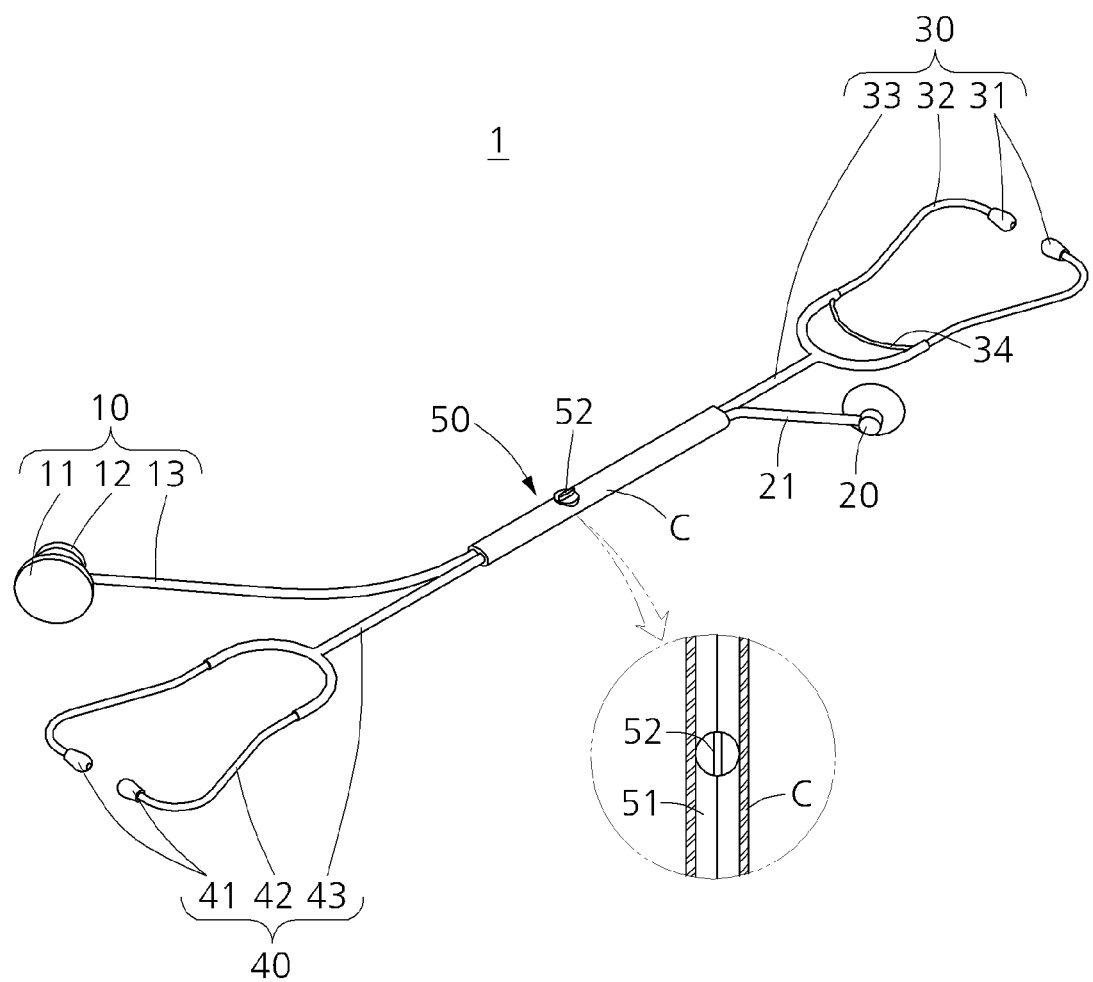
FIG. 1 is a perspective view of a stethoscope according to an exemplary embodiment of the inventive concept.

Referring to FIG. 1, a stethoscope 1 according to an exemplary embodiment of the inventive concept includes a chestpiece 10, a microphone unit 20, a first headset unit 30, a second headset unit 40 and a guiding unit 50.

The chestpiece 10 is used to auscultate for the inside of human body while contacting the patient on the body. Specifically, the chestpiece 10 is used to examine the patient by listening to the internal sound of the body, for example, heart sound, breath sound, artery sound, intestine sound, and blood vessel sound. Also, the chestpiece 10 contacts the patient to listen to brachial artery sound when measuring blood pressure. Such the chestpiece 10 includes a diaphragm 11 prepared at one side and a bell 12 prepared at the opposite side of the diaphragm 11.

The diaphragm 11 includes a flat plastic vibrating plate and lets the auscultation sound of frequency 100 Hz to 1 KHz, for example, lung sound or intestine sound, be heard. The bell 12 has a bell shape and lets the auscultation sound of frequency 20 Hz to 200 Hz, for example, comparatively low sound such as opening and shutting sounds of valves of the heart and swirl and backward flow sounds of blood flow. That is, the diaphragm 11 and the bell 12 auscultate for sounds of each different frequencies to examine the patient exactly.

As a guide, the reason that the diaphragm 11 and the bell 12 auscultate for sounds of each different frequencies is due to the structure of sound collecting position. Specifically, the bell 12 may auscultate for sounds of low frequency because it has no vibrating plate so that the vibration sound generated from a body may vibrate air directly. On the other hand, the diaphragm 11 delivers vibration of skin through plastic vibrating plate so that the vibrating of the vibrating plate may vibrate air to deliver the sound. At this time, the sound of low frequency may not be delivered any more when being absorbed to the vibrating plate, therefore, the diaphragm 11 may auscultate for the sound of high frequency when the sound has more than a predetermined vibration.

The auscultation sound gathered by the diaphragm 11 and the bell 12 is delivered through the air, for that, the diaphragm 11 and the bell 12 are connected to auscultating tube 13. The auscultating tube 13 is a path for the auscultation sound formed of flexible material.

The microphone unit 20 receives the doctor's voice. More desirably, the microphone unit 20 is for delivering the doctor's voice to the patient who has low hearing ability, which has a similar sound collecting function with the chestpiece 10 described above. The doctor's voice gathered through the microphone unit 20 is transferred through the microphone tube 21 formed of flexible material.

Meanwhile, the microphone unit 20 includes on/off functions, thereby being capable of perform modified examples of operating selectively.

The first headset unit 30 enables the doctor to listen to the auscultation sound collected by the chestpiece 10. The first headset unit 30 includes a pair of first ear pieces 31 for the doctor's ears, a pair of first binaurals 32 extended from the first ear pieces 31, and a first headset tube 33 extended so as to be connected to the first binaurals 31.

The ear pieces 31 are bent along the direction of external auditory meatus so as to be inserted and contacted to the doctor's ears. Such the first binaurals 31 are preferred to be formed of material being flexible and harmless to humans to provide comfort even in the state of being inserted to ears for a long time.

The first binaurals 32 are a kind of tubes connected from the first earpieces 31. Such the first binaurals 32 deliver the auscultation sound transferred through the first headset tube 33 connected through the auscultating tube 13, which are made of metal such as reinforced aluminum, steel, or copper.

The first headset tube 33 are made of flexible material like the auscultating tube 13 and the microphone tube 21 described above and performs a function of pathway for the auscultation sound.

The second headset unit 40 enables the patient to listen to the auscultation sound or the doctor's voice by being connected to any one of the chestpiece 10 and the microphone unit 20. The second headset unit 40 includes a pair of second earpieces 41, a pair of second binaurals 42, and the second headset tube 43 like the first headset unit 30. The second earpieces 41, the second binaurals 42, and the second headset tube 43 have similar structures with the first earpieces 31, the first binaurals 32, and the first headset tube 33 of the first headset unit 30, and detailed descriptions thereof will be omitted accordingly.

The second headset unit 40 has a function of delivering the doctor's voice or the auscultation sound to a patient having low hearing ability. Accordingly, a patient having low hearing ability may listen to the doctor's voice and the auscultation sound effectively.

The auscultating tube 13, the microphone tube 21, the first headset tube 33 and the second headset tube 43 are formed of flexible material so as to be transformed, accordingly, shapes and lengths thereof are not restricted to the examples.

Meanwhile, the chestpiece 10 and the second headset unit 30 are prepared to be extended in one direction, and the microphone unit 20 and the second headset unit 40 are prepared to be extended in other direction which is the opposite direction of the one direction. At this time, the auscultating tube 13, the microphone tube 21, the first headset tube 33 and the second headset tube 43 are tied by a cover C, and the cover C has a length of being enough to support the auscultating tube 13, the microphone tube 21, the first headset tube 33, and the second headset tube 43. Such the structure enables the doctor to examine a patient while wearing the first headset unit 30 opposing the chestpiece 10 on the ears and the patient to listen to the doctor's voice through the second headset unit 40 delivered from the microphone unit 20 positioned on the doctor's side.

The guide unit 50 guides the chestpiece 10 and the microphone unit 20 to be each connected to any one of the first headset unit 30 and the second headset unit 40. For that, the guide unit 50 includes a lever body 51 and an adjusting lever 52.

The lever body 51 is installed between the chestpiece 10 and the microphone unit 20 and between the first headset unit 30 and the second headset unit 40. The lever body 51 is a shape of two tubes like "II" parallel with each other, which is connected to the ausultating tube 13 and the microphone tube 21, and to the first headset tube 33 and the second headset tube 43 in parallel by each terminal. At this time, the auscultating tube 13 and the second headset tube 43 are connected to the one side of the lever body 51 in a row, and the microphone tube 21 and the first headset tube 33 are connected to the other side of the lever body 51 in a row. The inside of the lever body 51 is formed as a through hole such that a pathway for the doctor's voice and the auscultation sound may be provided.

The lever body 51 is prepared inside of the cover C covering the auscultating tube 13, the microphone tube 21, the first headset tube 33, and the second headset tube 43.

The adjusting lever 52 is installed inside of the lever body 51 and connects the first headset unit and the second headset unit 40 to any one of the chestpiece 10 and the microphone unit 20 respectively according to the rotating position. Here, the adjusting lever 52 has a form of being extended from the outside of the lever body 51 to the inside thereof so as to grip the adjusting lever 52 from the outside of the lever body 51. Accordingly, the position of the adjusting lever 52 may be changed while a user grips and rotates the adjusting lever 52.

Figure 2:
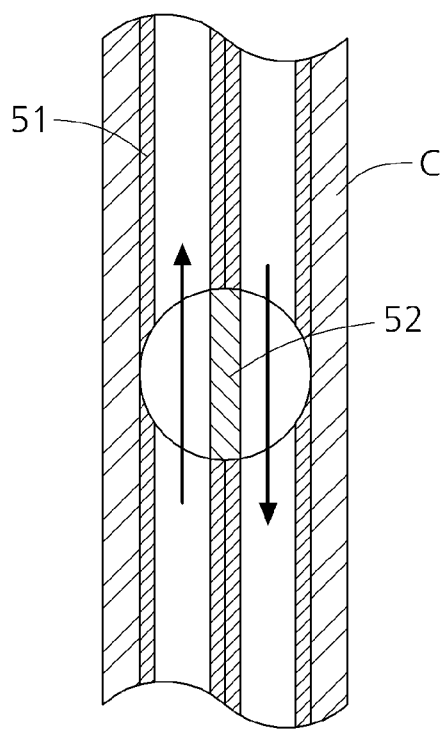
FIGS. 2 and 3 are schematic plan views illustrating the operation of the guiding unit shown in FIG. 1.
Figure 3:
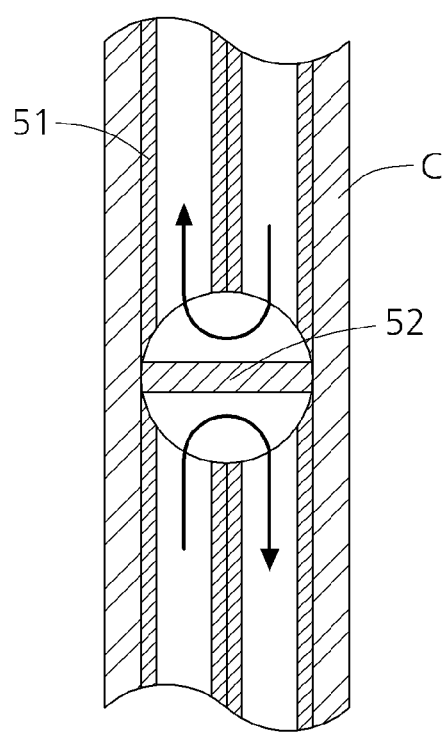

Meanwhile, according to an exemplary embodiment of the inventive concept, the adjusting lever 52 is rotatable between a first position connecting the chestpiece 10 and the first headset unit 30, and the microphone unit 20 and the second headset unit 40 at the same time as shown in FIG. 2, and a second position connecting the chestpiece 10 and the second headset unit 40, and the microphone unit 20 and the first headset unit 30 at the same time as shown in FIG. 3. Such the structure of the adjusting lever 52 enable the auscultation sound auscultated through the chestpiece 10 to be delivered to the doctor's ear through the first headset unit 30 or to the patient's ear through the second headset unit 40.

According to another exemplary embodiment, the auscultating operation of the stethoscope 1 according to the exemplary embodiment of the inventive concept will be described referring to FIG. 1 through FIG. 3.

A doctor contacts any one of the diaphragm 11 or the bell 12 of the chestpiece 10 on the body of a patient while wearing the first earpieces 31 of the first headset unit 30. The auscultation sound auscultated through the chestpiece 10 is delivered to the first headset unit 30 mutually connected by the first position of the adjusting lever 52 of the guiding unit 50 as shown in FIG. 2, thereby being listened by the doctor's ears. At this time, the doctor's voice delivered through the microphone unit 20 may be delivered to the patient through the second headset unit 40 connected through the microphone unit 20.

Meanwhile, in the case that the patient, not the doctor, wants to listen to the auscultation sound, the adjusting lever 52 may be rotated to the R direction with respect to the lever body 51 while being gripped by a user. The rotation of the adjusting lever 52 to the second position blocks connection of the chestpiece 10 and the first headset unit 30, but the chestpiece 10 is connected to the second headset unit 40. Accordingly, the patient may listen to the auscultation sound through the second earpieces 41 of the second headset unit 40.

Figure 4:
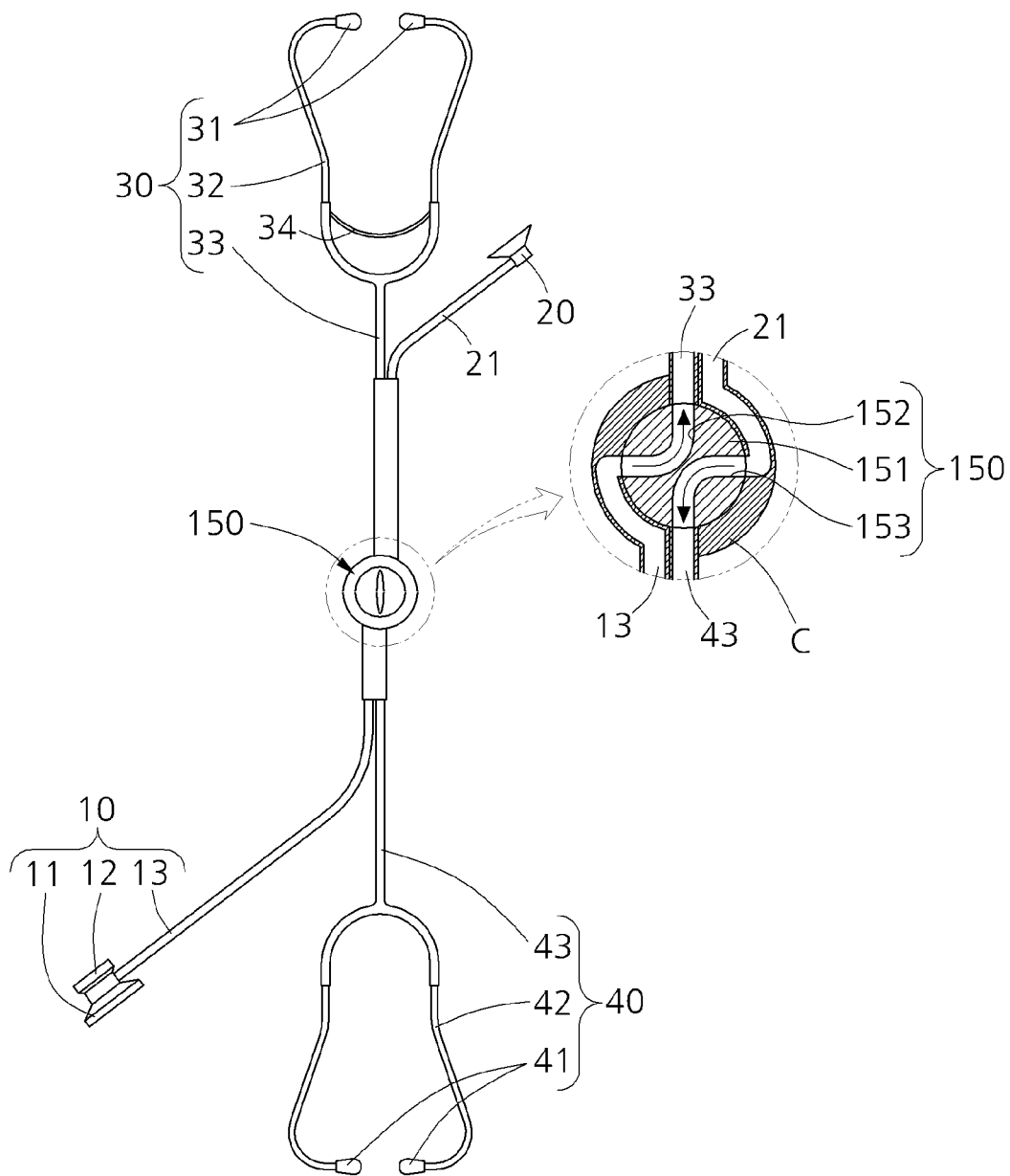
FIG. 4 is a schematic plan view of a guiding unit of a stethoscope according to another exemplary embodiment of the inventive concept.

According to yet another exemplary embodiment of the inventive concept, a guiding unit 150 of a stethoscope 1 is shown in FIG. 4. The stethoscope 1 includes a chestpiece 10, a microphone unit 20, a first headset unit 30, and a second headset unit 40, which has the same composition with the first exemplary embodiment, accordingly, detailed description will be omitted.

The guiding unit 150 includes a connecting member 151, a first guide line 152, and a second guide line 153 as shown in FIG. 4.

The connecting member 151 is prepared to be rotatable among the chestpiece 10, the microphone unit 20, the first headset unit 30, and the second headset unit 40. The connecting member 151 has a shape of a cylinder and rotates among the chestpiece 10, the microphone unit 20, the first headset unit 30, and the second headset unit 40. At this time, an auscultating tube 13 and a second headset tube 43 are connected to one side of the connecting member 151 and a microphone tube 21 and a first headset tube 33 are connected to the other side of the connecting member 151, which are covered with a cover C.

Figure 5:
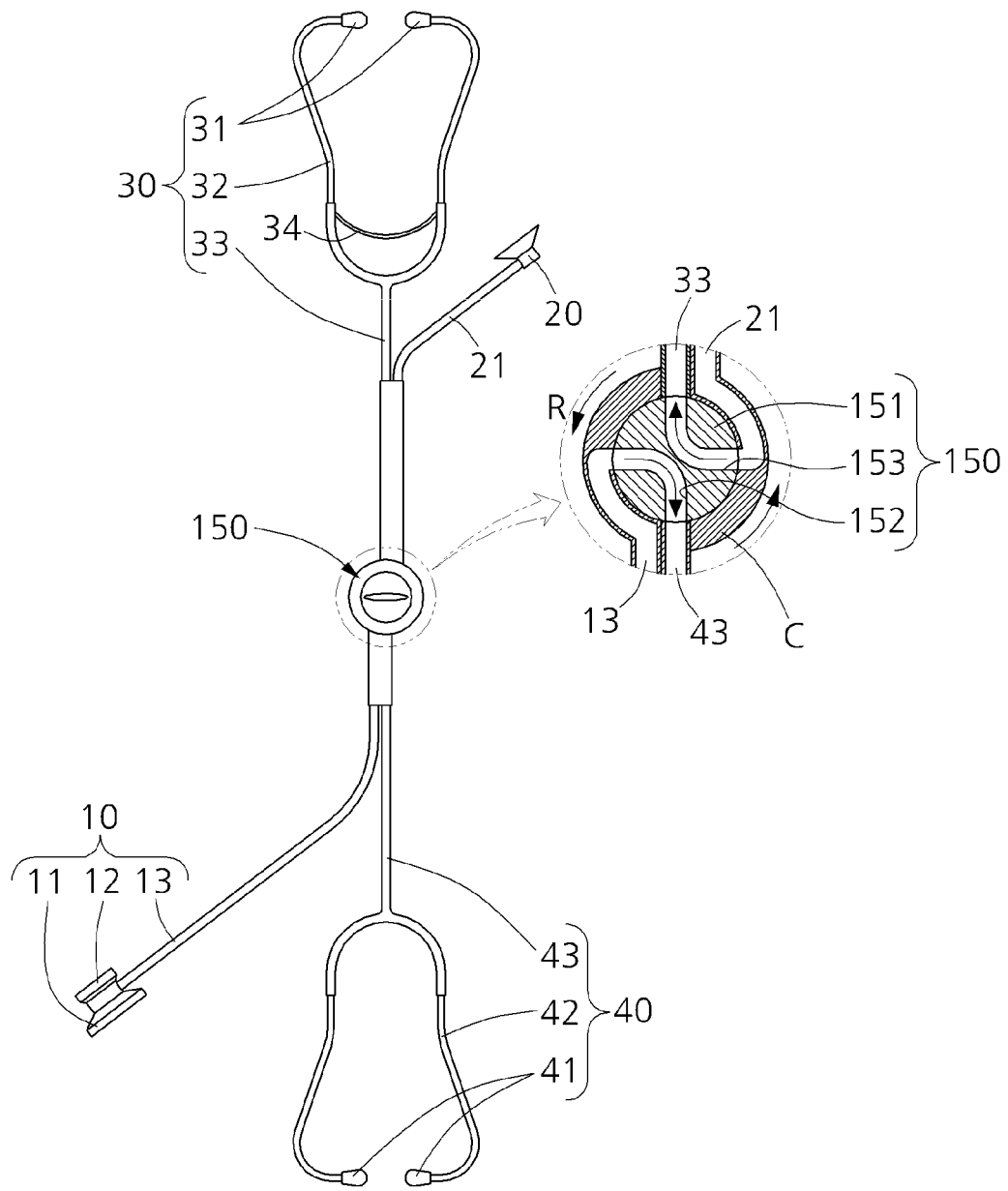
FIG. 5 is a schematic plan view illustrating the guiding unit according to the another exemplary embodiment shown in FIG. 4.

The first guide line 152 and the second guide line 153 are prepared inside of the connecting member 151 as a pathway for delivering mutually separated auscultation sounds or doctor's voice. More specifically, the first guide line 152 and the second guide line 153 are prepared inside the connecting member 151 while being divided so as to connect the chestpiece 10 and the first headset unit 30 and connect the microphone unit 20 and the second headset unit 40 mutually as shown in FIG. 4 according to the rotating position, or connect the chestpiece 10 and the second headset unit 40, and the microphone unit 20 and the first headset unit 30 as shown in FIG. 5 in mutual alternation. Such the first guide line 152 and the second guide line 153 have a bended form like the Korean letter "¬" and guide progress of the auscultation sound and the doctor's voice.

According to still yet another exemplary embodiment of the inventive concept, the operation of the stethoscope 1 and the guiding unit 150 according to the second exemplary embodiments will be described referring to FIGS. 4 and 5.

As shown in FIG. 4, the first guide line 152 mutually connects the auscultating tube 13 of the chestpiece 10 and the first headset tube 33 of the first headset unit 30, and the second guide line 153 mutually connects the microphone tube 21 of the microphone unit 20 and the second headset tube 43 of the second headset unit 40. Accordingly, the doctor may listen to the auscultation sound of the chestpiece 10 through the first headset unit 30, and the patient may listen to the doctor's voice from the microphone unit 20 through the second headset unit 40.

Meanwhile, the first guide line 152 mutually connects the auscultating tube 13 of the chestpiece 10 and the second headset tube 43 of the second headset unit 40 when the connecting member 151 rotates to the R direction as shown in FIG. 5. Accordingly, even the patient may listen to the auscultation sound delivered through the chestpiece 10.

Figure 6:
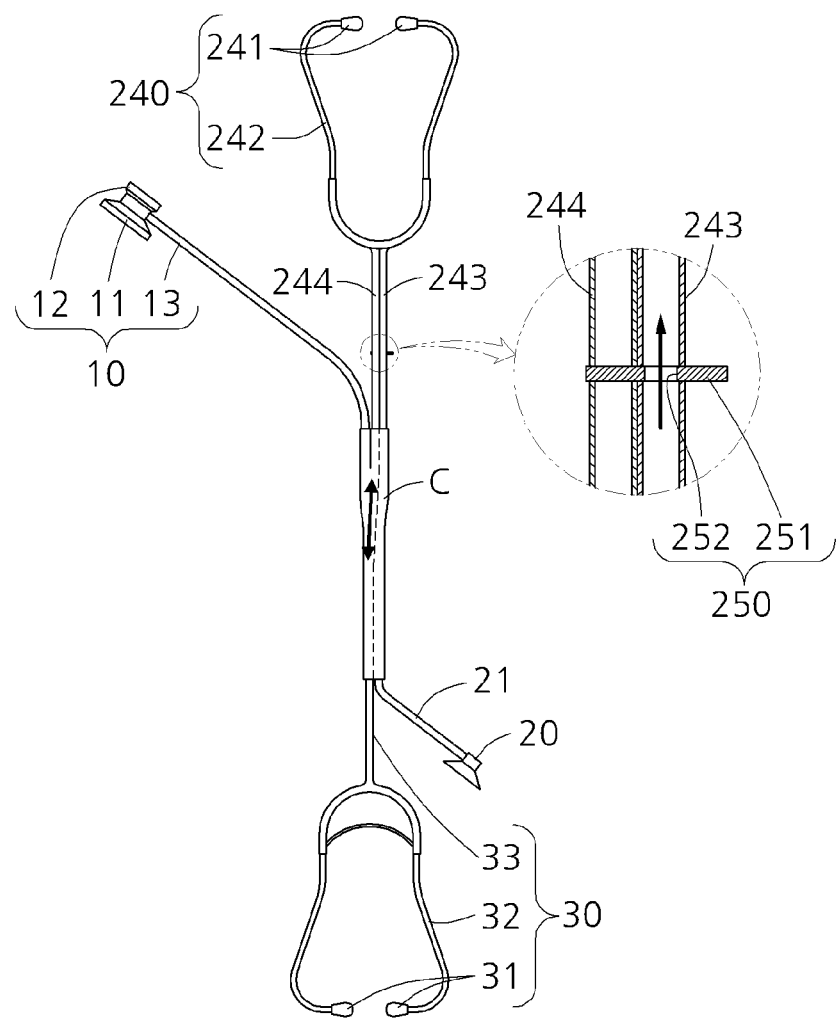
FIG. 6 is a schematic plan view of a guiding unit of a stethoscope according to yet another exemplary embodiment of the inventive concept.
Figure 7:
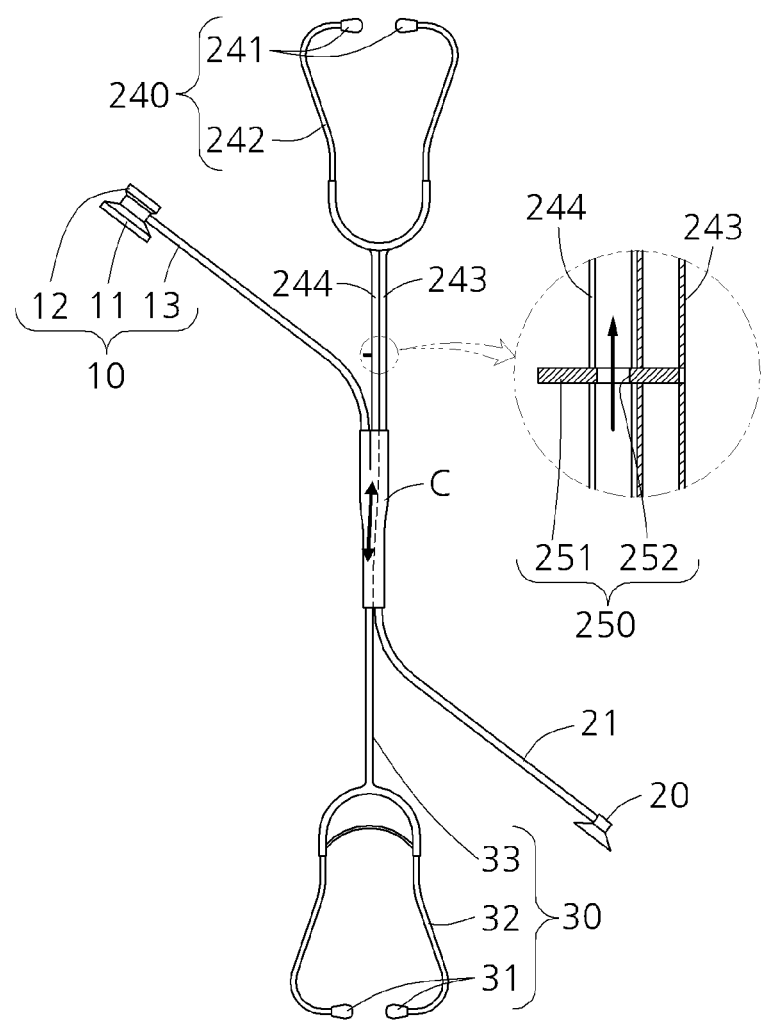
FIG. 7 is a schematic plan view illustrating the guiding unit according to the yet another exemplary embodiment shown in FIG. 6.

According to still yet another exemplary embodiment of the inventive concept, a stethoscope 1 and a guiding unit 250 according to a third exemplary embodiment of the inventive concept are shown in FIGS. 6 and 7.

Referring to FIG. 7, a chestpiece 10, a microphone unit 20, and a first headset unit 30 of the stethoscope 1 according to the third exemplary embodiment have same composition to those of the first exemplary embodiment. Also, a pair of second earpieces 241 and a pair of second binaurals 242 of the second headset unit 240 according to the third exemplary embodiment have same composition to those of the first exemplary embodiment, accordingly, detailed descriptions will be omitted.

Meanwhile, the second headset unit 240 is connected to an auscultation tube 13 of the chestpiece 10 and a microphone tube 21 of the microphone unit 20 through a first connecting tube 243 and a second connecting tube 244. Specifically, the first connecting tube 243 is connected to the microphone tube 21, and the second connecting tube 244 is connected to the auscultating tube 13 and the first headset tube 33.

A connecting body C is prepared for connecting the first connecting tube 243, the second connecting tube 244, the auscultating tube 13, the microphone tube 21, and the first headset tube 33. One side of the connecting body C is connected to the auscultating tube 13, the first connecting tube 243, and the second connecting tube 244, and the other side thereof is connected to the microphone tube 21 and the first headset tube 33. At this time, the auscultating tube 13, the second connecting tube 244, and the first headset tube 33 are mutually connected through the connecting body C, and the divided first connecting tube 243 is connected to the microphone tube 21.

The guiding unit 250 is prepared between the first connecting tube 243 and the second connecting tube 244 so as to be movable such that only any one of the first connecting tube 243 and the second connecting tube 244 may be opened. More specifically, the guiding unit 250 includes a guide body 251 installed between the first connecting tube 243 and the second connecting tube 244 so as to be movable and a guide hole 252 formed through the guide body 251. At this time, a part of the guide body 251 is prepared to be exposed outside from the first connecting tube 243 and the second connecting tube 244, which may be operated by a user.

As shown in FIG. 6, the first connecting tube 243 and the second connecting tube 244 connected to the second headset unit 240 are connected to the auscultating tube 13 and the microphone tube 21, and the guide hole 252 prepared in the guide body 251 of the guiding unit 250 is opening the first connecting tube 243. At this time, the opening of the first connecting tube 243 enable the patient to listen to the doctor's voice by being connected to the microphone tube 21.

On the other hand, the guide body 251 of the guiding unit 250 may be moved between the first connecting tube 243 and the second connecting tube 244, accordingly, the guide hole 252 may be moved to open the second connecting tube 244 as shown in FIG. 7. Accordingly, the patient may listen to the auscultation sound provided through the chestpiece 10 by connecting the second headset unit 240 and the auscultating tube 13. At this time, the doctor may listen to the auscultation sound through the auscultating tube 13 and the first headset tube 33 mutually connected.

While the present invention has been particularly shown and described with reference to exemplary embodiments thereof, it will be understood that various changes in form and details may be made therein without departing from the spirit and scope of the following claims.

INDUSTRIAL USABILITY

The present invention is applicable to a stethoscope.

What is claimed is:

1. A stethoscope comprising:
a chestpiece for auscultating a patient by contacting a body of the patient, and connected to an auscultating tube configured to deliver an auscultation sound auscultated by the chestpiece;
a microphone unit configured to receive a doctor's voice, and connected to a microphone tube configured to deliver the doctor's voice;
a first headset unit configured for the doctor to listen to the auscultation sound auscultated by the chestpiece, and connected to a first headset tube configured to deliver the auscultation sound to the first headset unit;
a second headset unit configured for the patient to listen to the auscultation sound, and connected to a second headset tube configured to deliver the auscultation sound or the doctor's voice to the second headset, wherein the microphone tube and the first headset tube are tied into a bundle such that the microphone unit is placed at a position adjacent to the first headset unit; and
a guiding unit including a single movable member provided inside the guiding unit and configured to guide the auscultation sound from the auscultating tube to the first headset tube while guiding the doctor's voice from the microphone tube to the second headset tube at a first position, and configured to guide the auscultation sound from the auscultating tube to the second headset tube while guiding the doctor's voice from the microphone tube to the first headset tube at a second position.

2. The stethoscope of claim 1, wherein the guiding unit comprises:
a lever body installed among the chestpiece, the first headset unit, and the second headset unit, wherein the auscultating tube, the microphone tube, the first headset tube, and the second headset tube are directly connected to the lever body; and
an adjusting lever prepared, as the single movable member, in the lever body so as to be rotatable to connect the chestpiece and the first headset unit or the chestpiece and the second headset unit according to a rotating position of the adjusting lever.

3. The stethoscope of claim 1, wherein the guiding unit comprises:
a single connecting member prepared, as the single movable member, among the chestpiece, the first headset unit, and the second headset unit so as to be rotatable, wherein the auscultating tube, the microphone tube, the first headset tube, and the second headset tube are directly connected to the single connecting member; and
a first guide line and a second guide line prepared inside the single connecting member in each section separately and connecting the chestpiece and the first headset unit or the chestpiece and the second headset unit in alternation according to a rotating position of the single connecting member.

4. A stethoscope comprising:
a chestpiece for auscultating a patient by contacting a body of the patient, and connected to an auscultating tube configured to deliver an auscultation sound auscultated by the chestpiece;

a microphone unit configured to receive a doctor's voice, and connected to a microphone tube configured to deliver the doctor's voice;

a first headset unit configured to be connectable to the doctor's or another doctor's ears, and connected to a first headset tube configured to deliver the auscultation sound to the first headset unit;

a second headset unit configured to be connectable to the patient's ears, and connected to a second headset tube configured to deliver the auscultation sound or the doctor's voice to the second headset, wherein the microphone tube and the first headset tube are tied into a bundle such that the microphone is placed at a position adjacent to the first headset unit; and a guiding unit including a single movable member guiding the auscultation sound from the chestpiece to the first headset unit only while guiding the doctor's voice from the microphone unit to the second headset unit only at a first operation position, and guiding the auscultation sound from the chestpiece to the second headset unit only while guiding the doctor's voice from the microphone unit to the first headset unit only at a second operation position.

5. The stethoscope of claim 4, wherein the guiding unit comprises: a lever body installed among the chestpiece, the microphone unit, the first headset unit, and the second headset unit, wherein the auscultating tube, the microphone tube, the first headset tube, and the second headset tube are directly connected to the lever body; and an adjusting lever installed, as the single movable member, in the lever body which is rotatable between the first operation position such that the chestpiece and the first headset unit are connected, and the microphone unit and the second headset unit are connected and the second operation position such that the chestpiece and the second headset unit are connected, and the microphone unit and the first headset unit are connected.

6. The stethoscope of claim 4, wherein the guiding unit comprises:

a single connecting member installed, as the single movable member, among the chestpiece, the microphone unit, the first headset unit, and the second headset unit so as to be rotatable, wherein the auscultating tube, the microphone tube, the first headset tube, and the second headset tube are directly connected to the single connecting member; and a first guide line and a second guide line prepared inside the single connecting member in each section separately and connecting the chestpiece and the first headset unit, and the microphone unit and the second headset unit at the first operation position, and connecting the chestpiece and the second headset unit, and the microphone unit and the first headset unit at the second operation position.

* * * * *